(12) United States Patent
Qiu

(10) Patent No.: US 7,638,650 B2
(45) Date of Patent: Dec. 29, 2009

(54) FLUOROALKYL SURFACTANTS

(75) Inventor: Weiming Qiu, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 196 days.

(21) Appl. No.: 11/890,376

(22) Filed: Aug. 6, 2007

(65) Prior Publication Data
US 2009/0043130 A1    Feb. 12, 2009

(51) Int. Cl.
| | |
|---|---|
| C07C 243/14 | (2006.01) |
| C07C 233/00 | (2006.01) |
| C07C 235/00 | (2006.01) |
| C07C 237/00 | (2006.01) |
| C07C 215/00 | (2006.01) |
| C07C 217/00 | (2006.01) |
| C07C 211/00 | (2006.01) |
| B01F 17/00 | (2006.01) |

(52) U.S. Cl. ............ 564/151; 564/159; 564/160; 564/201; 564/203; 564/209; 564/464; 564/503; 564/504; 564/505; 564/506; 564/507; 564/511; 564/512; 516/201; 516/203

(58) Field of Classification Search .......... None
See application file for complete search history.

(56) References Cited

U.S. PATENT DOCUMENTS

| | | | |
|---|---|---|---|
| 3,227,761 | A | 1/1966 | DeBrunner et al. |
| 3,621,059 | A | 11/1971 | Bartlett |
| 3,692,843 | A | 9/1972 | Resnick |
| 3,944,610 | A | 3/1976 | Caporiccio et al. |
| 4,098,811 | A | 7/1978 | Falk |
| 4,855,025 | A | 8/1989 | Gautier et al. |
| 5,035,841 | A | 7/1991 | Costello et al. |
| 5,066,672 | A | 11/1991 | Sismondi et al. |
| 5,482,822 | A | 1/1996 | Mihara et al. |
| 6,054,492 | A | 4/2000 | Kabanov et al. |
| 7,164,041 | B1 | 1/2007 | Moore et al. |
| 2005/0175867 | A1 | 8/2005 | Adachi et al. |
| 2005/0197273 | A1 | 9/2005 | Savu et al. |
| 2006/0148671 | A1 | 7/2006 | Dams et al. |
| 2007/0049646 | A1 | 3/2007 | Moore et al. |
| 2008/0113172 | A1 | 5/2008 | Acosta et al. |
| 2008/0113573 | A1 | 5/2008 | Acosta et al. |

FOREIGN PATENT DOCUMENTS

| | | |
|---|---|---|
| CA | 892067 | 8/1970 |
| CN | 1692974 | 3/2005 |
| DE | 265398 | 3/1987 |
| EP | 0 144 844 A2 | 6/1985 |
| EP | 0 193 202 | 9/1986 |
| EP | 0 144 844 B1 | 2/1989 |
| EP | 0 396 962 | 11/1990 |
| FR | 1470669 | 3/1966 |
| FR | 2623497 | 11/1987 |
| GB | 1097679 | 1/1968 |
| JP | 53045684 | 4/1978 |
| JP | 55007818 | 1/1980 |
| JP | 59228071 | 6/1983 |
| SU | 1398880 | 3/1985 |
| WO | 97/49675 A1 | 12/1997 |
| WO | WO 2005/113488 A1 | 12/2005 |

OTHER PUBLICATIONS

Bückman et al., Functionalization of Poly(ethylene glycol) and Monomethoxy-Poly(ethylene glycol); Makromol. Chem. (1981), 182(5), 1379-1384.
Mathis et al., A Novel Class of Nonionic Microemulsions: Fluorocarbons in Aqueous Solutions of Fluorinated Poly(oxyethylene) Surfactants; J. Am. Chem. Soc. (1984), 106, 6162-6171.
Afzal et al., Synthesis of Perfluoroalkyl-N-Polyethoxylated Amides; J. of Fluorine Chemistry (1987), 34(3-4), 385-393.
Ravey et al., Phase and structure behavior of fluorinated nonionic surfactant systems; Progress in Colloid & Polymer Science (1987), 73, 127-133.
Selve et al., Monodisperse perfluoro-polyethoxylated amphiphilic compounds with two-chain polar head—preparation and properties; Tetrahedron (1991), 47(3), 411-428.
Myrtil et al., Double-tailed perfluoroalkyl telomeric surfactants derived from tris(hydroxymethyl)acrylamidomethane for medical applications; Macromol. Chem. Phys. (1994), 195(4), 1289-1304.
Myrtil et al., Perfluoroalkylated telomers derived from tris(hydroxymethyl)acrylamidomethane as surfactants and co-surfactants in fluorocarbon emulsions: J. of Fluorine Chemistry (1995) 71(1), 101-105.

(Continued)

*Primary Examiner*—Brian J Davis
(74) *Attorney, Agent, or Firm*—Nancy S. Mayer

(57) ABSTRACT

A compound of formula (I):

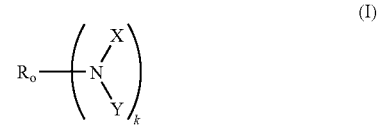

wherein k is 1 or 2;
Y is $-CH_2CH(CF_3)_2$ or $-(CH_2)_nC_F$;
X is hydrogen, $-(CH_2)_nR_f$, or $-C(O)[CF(A)]_p-B-R_f$, wherein B is a covalent bond, $-O-$ or $-(CH_2)_m-$; A is $-F$ or $-CF_3$; and each $R_f$ is independently $C_1$ to $C_6$ perfluorinated alkyl, optionally interrupted by one or more oxygens;
$R_o$ is $R_o^1$ or is an alkyl having from about 10 to about 100 carbon atoms, interrupted or substituted by one or more hydrophilic groups;
R is hydrogen or a $C_1$ to $C_4$ alkyl; and
$R_o^1$ is an aliphatic group of from about 10 to about 100 carbon atoms, interrupted by about from about 5 to about 50 ether oxygens;
provided that 1) when Y is $-(CH_2)_nR_f$, $R_o$ is $R_o^1$; 2) when X is hydrogen, Y is $-CH_2CH(CF_3)_2$; and 3) when X is $-(CH_2)_nR_f$ and Y is $-(CH_2)_nR_f$, $R_o$ is $R_o^1$.

13 Claims, No Drawings

OTHER PUBLICATIONS

Guittard et al., Convenient Synthesis of Monodisperse Fluorinated Nonionic Surfactants Containing Two Hydrophilic Hydroxylated Moieties; Tetrahedron Letters (1995), 36(43), 7863-7866.

Guittard et al., Synthesis and Behavior at the Air-Water Interface of Fluorinated Nonionic Surfactants Containing Two Methylated Polyoxyethylene Moieties; J. of Colloid and Interface Science (1996), 177(1), 101-105.

Dos Santos Afonso et al., Kinetics and mechanism of thermal gas-phase oxidation of hexafluoroporopene in the presence of trifluoromethylhypofluorite, $CF_3OF$; Physical Chemistry Chemical Physics (2000), 2(7), 1393-1399.

Rocaboy et al., Convenient Syntheses of a Family of Easily Recoverable Fluorous Primary, Secondary, and Tertiary Aliphatic Amines $NH_{3-+}[(CH_2)_m(CF_2)_7CF_3]+$ (m =3-5; +=1-3)—Fine Tuning of Basicities and Fluorous Phase Affinities; Eur. J. Org. Chem. (2000), 2621-2628.

Abstract—Gonek et al., Synthesis of ethoxylated amides of perfluoroalphiphatic acids; Fluorine Notes (2001), 14 (no page given).

Mohamed Allouch et al: "Nonionic amphiphilic compounds from aspartic and glutamic acids as structural mimics of lecithins" Journal of the American Oil Chemists' Society, vol. 73, No. 1, 1996, pp. 87-96, XP002503356.

Floryan De Campo et al: "Copper(I) complexes mediated cyclization reaction of unsaturated ester under fluoro biphasic procedure", Journal of Organic Chemistry, vol. 64, 1999, pp. 4969-4971, XP002503126.

FLUOROALKYL SURFACTANTS

FIELD OF INVENTION

The field of invention is fluorinated surfactants and their synthesis and use.

BACKGROUND OF INVENTION

For surfactants and surface treatment agents with fluorochemical chains longer perfluoroalkyl chains contain a higher percentage of fluorine at a given concentration and provide better performance. However, fluorinated materials are more expensive. Reduction of the fluorine content with delivery of the same or higher performance is therefore desirable. Reducing the fluorine content would reduce the cost, but it is necessary to maintain product performance.

U.S. Pat. No. 3,621,059 discloses amides derived from hexafluoropropylene oxide polymer acids and monoamine terminated polyalkylene oxide, that function as surfactants and emulsifying agents. These compounds contain a single perfluoroalkyl chain which was exemplified as containing eight or more carbon atoms.

It is desirable to improve surfactant or surface treating agent performance and to increase the fluorine efficiency, i.e., boost the efficiency or performance of the surfactants or treating agents so a lower proportion of the expensive fluorine component is required to achieve the same level of performance, or to have better performance using the same level of fluorine.

SUMMARY OF INVENTION

The present invention comprises a compound of formula (I):

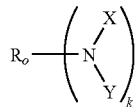

wherein
k is 1 or 2;
Y is —$CH_2CH(CF_3)_2$ or —$(CH_2)_nR_f$;
X is hydrogen, —$(CH_2)_nR_f$, or —$C(O)[CF(A)]_p$-B—$R_f$;
B is a divalent radical selected from the group consisting of a covalent bond, —O— and —$(CH_2)_m$—;
m is an integer of 1 to about 10;
p is an integer of 0 or 1, with the proviso that when p is 0, B is a covalent bond or —$(CH_2)_m$—;
n is an integer of from about 3 to about 10;
A is —F or —$CF_3$;
each $R_f$ is independently $C_1$ to $C_6$ perfluorinated linear or branched alkyl, optionally interrupted by one or more oxygens;
$R_o$ is $R_o^1$ or is a linear or branched alkyl having from about 10 to about 100 carbon atoms, interrupted or substituted by one or more hydrophilic groups selected from the group consisting of —O—, —OH, —NR—, —N(R)$_2$, and —C(O)NR—, wherein a) the ratio of hydrophilic groups to carbon atoms is from about 1:2 to about 1:10; b) each carbon atom has at most one hydrophilic group bonded to it, and c) covalent bonding between hydrophilic groups is absent;
R is hydrogen or a $C_1$ to $C_4$ linear or branched alkyl; and
$R_o^1$ is a linear or branched aliphatic group of from about 10 to about 100 carbon atoms, interrupted by about from about 5 to about 50 ether oxygens, wherein a) the ratio of ether oxygen to carbon atoms is from about 1:2 to about 1:3, b) each carbon atom has at most one ether oxygen atom bonded to it, and c) covalent bonding between ether oxygen atoms is absent;
provided that
1) when Y is —$(CH_2)_nR_f$, $R_o$ is $R_o^1$;
2) when X is hydrogen, Y is —$CH_2CH(CF_3)_2$; and
3) when X is —$(CH_2)_nR_f$ and Y is —$(CH_2)_nR_f$, $R_o$ is $R_o^1$.

The present invention further comprises a method of lowering surface tension of a medium comprising contacting the medium with a composition of formula (I), as defined above.

The present invention further comprises a process for fluoroalkylation of a primary amine comprising contacting the primary amine with hexafluoroisobutylene to provide a secondary fluoroalkylamine having a hexafluoroisobutyl radical covalently bonded to the amine.

DETAILED DESCRIPTION

Herein all trademarks are designated with capital letters. All patents cited herein are hereby incorporated by reference.

One aspect of the invention is a compound of formula (I):

wherein $R_o$, X, Y, and k are as disclosed above.

$R_o$ is a monovalent (when k=1) or divalent (when k=2) linear, or branched aliphatic, or cycloaliphatic radical, as disclosed above, that is typically covalently linked to a primary monoamine, for instance, $R_oNH_2$, or a primary diamine, for instance, $R_o(NH_2)_2$. Alternatively $R_o$ can be derived from another group that can be converted to monoamine or a diamine, for instance, a halide or tosylate; or a bis-halide or bis-tosylate.

In one preferred embodiment of formula (I) the radical $R_o$ is $R_o^1$, herein defined as a linear or branched aliphatic group of from about 10 to about 100 carbon atoms, interrupted by from about 5 to about 50 ether oxygens, and more preferably from about 20 to about 40 carbon atoms interrupted by from about 5 to about 20 ether oxygens, wherein the ratio of ether oxygen atoms to carbon atoms is from about 1:2 to about 1:4; and more preferably, from about 1:2 to about 1:3; and wherein each carbon atom has at most one ether oxygen atom bonded to it, and covalent bonding between ether oxygen atoms is absent. In this embodiment, preferably $R_o^1$ has a molecular weight, when each valency is occupied by an —$NH_2$ group, of between about 200 and about 2200, and a solubility in water of 1 weight %, and more preferably 5 weight %, or higher. $R_o^1$ radicals can be derived from the reaction of amine-terminated polyoxyalkylenes. The preference for the radical $R_o$ equal to $R_o^1$, is applicable to all other embodiments, including those of formulas (II), (III), (IV), (VI) and (VII) described below.

Amine-terminated polyoxyalkylenes useful in the formation of compositions of formula (I) wherein $R_o$ is $R_o^1$ and k is 1, include amine-terminated polyethylene glycol monomethyl ether (mPEGNH$_2$) or amine terminated polyethylene glycol-polypropylene glycol-polyethylene glycol triblock monomethyl ether (mPEG-PPG-PEG-NH$_2$). They are available by treatment of corresponding hydroxyl terminated monomethyl ethers with thionyl bromide followed by treatment with ammonia as described by Bückmann et al (Makromol. Chem. 182, p. 1379-1384, 1981). In a similar manner amine terminated monomethyl ethers of random copolymers of ethylene oxide and propylene oxide are also available. Commercial examples of these materials are JEFFAMINE® polyoxyalkyleneamines XTJ-505, and XTJ-506 from Huntsman Chemical, The Woodlands, Tex., and a development sample XTJ-580, also known as SURFONAMINE L-55, also from Huntsman Chemical.

Other amine-terminated polyoxyalkylenes useful in the formation of compositions of formula (I), wherein $R_o$ is $R_o^1$ and k is 2, include amine terminated polyethylene glycol ethers ($NH_2$-PEG-$NH_2$), amine terminated polyethylene glycol-polypropylene glycol-polyethylene glycol triblock ethers ($NH_2$-PEG-PPG-PEG-$NH_2$), amine terminated polypropylene glycol-polyethylene glycol-polypropylene glycol triblock ethers ($NH_2$-PPG-PEG-PPG-$NH_2$), and amine terminated random copolymers of ethylene oxide and propylene oxide. They are available by synthesis by treatment of the corresponding hydroxy terminated polymers with thionyl chloride and ammonia. Commercial examples of these materials are JEFFAMINE® polyoxyalkyleneamines ED-600 (XTJ-500, MW 600), ED-900 (XTJ-501, MW 900), ED-2003 (XTJ-502, MW 2000), and HK-511 (MW 220) available from Huntsman Chemical, The Woodlands, Tex.

Preferably the amine-terminated polyoxyalkylenes have from about 5 to about 20 repeat units, and more preferably about 10 to about 20 repeat units. Preferred amine-terminated polyoxyalkylenes for preparing compositions of the invention have a water solubility of 1 weight %, and more preferably a water solubility of 5 weight %, or higher. These materials typically are predominately polyethylene glycol (PEG) based and are therefore more hydrophilic than polypropylene glycol (PPG) based materials.

Other embodiments of the invention include specific compounds of formula (I), designated as formulae (II), (III) and (IV) and illustrated in Scheme 1:

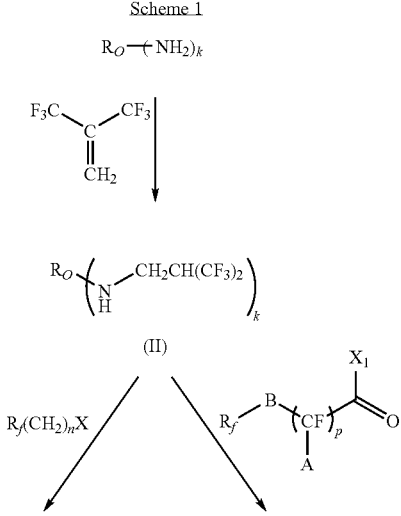

-continued

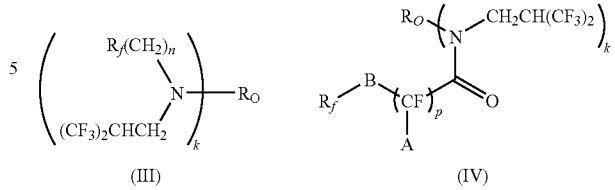

These compounds are defined by formula (I) wherein Y is —$CH_2CH(CF_3)_2$, and X is hydrogen, —$(CH_2)_nR_f$, and —$C(O)[CF(A)]_p$-B—$R_f$, respectively, and $R_o$, $R_f$, A, B, p and k are as defined above.

The present invention further comprises a process for fluoroalkylation of a primary amine comprising contacting the primary amine with hexafluoroisobutylene (HFIB), at a reaction temperature and reaction period sufficient to provide a secondary fluoroalkylamine having a hexafluoroisobutyl radical covalently bonded to the amine. Compositions of formula (II) are prepared by this method. The contacting can take place in the presence of a solvent and/or in the presence of a base catalyst. The term "primary amine" in referring to the above process, is defined herein to include monoamines and polyamines of formula $R_o^2(NH_2)_q$ wherein q is an integer of 1 to about 100; and $R_o^2$ is defined as a linear or branched alkyl, or cycloaliphatic radical, or a combination thereof, having 1 to about 100 carbon atoms, including radicals interrupted or substituted by one or more hydrophilic group(s) selected from the group consisting of: —O—, —OH, —NR—, —N(R)$_2$, and —C(O)NR—; provided that a sum of the primary amines, q, and the hydrophilic groups is no greater than the total number of carbon atoms in $R_o^2$; each carbon atom has at most one primary amine or hydrophilic group bonded to it, and covalent bonding between hydrophilic groups is absent. Preferred $R_o^2$ are wherein the ratio of hydrophilic groups, including the primary amines, to carbon atoms is from about 1:2 to about 1:10. Thus, the process allows addition of the hexafluoroisobutyl group to a wide variety of monoamines and polyamines. Examples of mono-primary amines useful in the process of the invention include: straight and branched chain alkyl amines such as methylamine, ethyl amine, propyl amine, isopropyl amine, butyl amine, isobutyl amine, 2-(N,N-dimethylamino)ethylamine, hexyl amine, octyl amine, nonyl amine; oxyalkylene amines such as amine terminated polyethylene glycol monomethyl ether (mPEGNH$_2$) and amine terminated polyethylene glycol-polypropylene glycol-polyethylene glycol triblock monomethyl ether (mPEG-PPG-PEG-NH$_2$) disclosed above. Examples of primary diamines useful in the process of the invention include: ethylene diamine, propylene diamine, diethylene triamine, and the oxyalkylene diamines NH$_2$-PEG-NH$_2$ and NH$_2$-PEG-PPG-PEG-NH$_2$, disclosed above.

The fluoroalkylation of the primary amine can be run in the presence or absence of solvent. Preferably a solvent is used. Suitable solvents for the method of the invention include alcohols, such as methanol and ethanol; alkyl ethers, such as tetrahydrofuran (THF), dioxane, and dimethoxyethane; alkyl esters such as ethyl acetate and butyl acetate; hydrocarbons such as xylenes, and toluene; halogenated hydrocarbons such as 1,2-dichloroethane and dichloromethane; nitriles such as acetonitrile; and amides such as dimethylformamide and dimethylacetamide (DMAc).

The fluoroalkylation of the primary amine can be run in the presence of a base catalysis, if so desired. Suitable catalysts include tertiary alkyl amines, such as triethyl amine; alkali metal hydroxides, such as sodium hydroxide and potassium hydroxide; and alkali metal hydrides, such as sodium hydride and potassium hydride.

The fluoroalkylation of the primary amine can be run in a pressure vessel to contain the hexafluoroisobutylene, or it can be run at atmospheric pressure using a coolant such as a carbon dioxide-solvent slurry to condense the hexafluoroisobutylene. In the latter case reactions are usually conducted at about 0° C. to about 40° C., and preferably at from about 10° C. to about 35° C.; for a time period of about, 0.1 to about 15 hours.

Compounds of formula (III) can be prepared by treating compounds of formula (II) with a perfluoroalkylalkylene halide or tosylate: $R_f(CH_2)_nX$, wherein X is a leaving group, preferably selected from bromide, iodide or tosylate, according to Scheme 1. $R_f(CH_2)_nI$, wherein n is 4 can be made by the procedure described in European Patent 193202.

Compounds of formula (IV) can be prepared by treating compounds of formula (II) with the fluoroalkyl carboxylic acid derivatives $X_1$—$C(O)[CF(A)]_p$-B—$R_f$, wherein $X_1$ is a leaving group selected from the group consisting of $C_1$ to $C_4$ linear or branched alkoxy; halides selected from fluoride and chloride; and $C_1$ to $C_4$ carboxylates; wherein p, A, B and $R_f$ are as described above; with the proviso that when p is O, B is a covalent bond or —$(CH_2)_m$—; wherein m is 1 to about 10. When $X_1$—$C(O)[CF(A)]_p$-B—$R_f$ is an acid halide, typically one equivalent or more of an organic base, such as pyridine or triethylamine is present during the treatment. Typically a nonhydroxylic hydrocarbon solvent such as toluene or xylenes or a halocarbon such as dichloromethane is used in the treatment.

Fluoroalkyl carboxylic acid derivatives, $X_1$—C(O)[CF(A)]$_p$-B—$R_f$, useful in preparation of compounds of formula (IV) include, when p is 0, 2H,2H,3H,3H-perfluorohexanoyl chloride, 2H,2H,3H,3H-perfluoroheptanoyl chloride, 2H,2H,3H,3H-perfluorononoyl chloride, perfluoroheptanoyl chloride, perfluoropentanoyl chloride, 2H,2H-perfluoropentanoyl chloride, 2H,2H-perfluorohexanoyl chloride, and 2H,2H-perfluorooctanoyl chloride. Other fluorinated carboxylic acid halides useful in the synthesis of compositions of formula (IV) include, when p is 1, the hexafluoropropylene oxide dimer (compound D1), available from E.I. du Pont de Nemours and Company, Wilmington, Del.; and the telomer acid fluoride, compound D2 wherein s is 1 to 4. The telomer acid fluorides including compound D2, wherein s is 1, are available by synthesis as disclosed in British Patent 1,097,679 and Afonso, et al, Phys. Chem. Chem. Phys., 2000, 2 1393-1399.

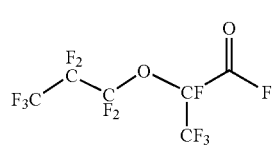

Compound D1

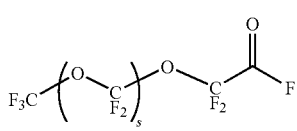

Compound D2

Other useful compounds are the branched telomer acid fluorides of formula D3, wherein v is 1 to 3, that are available by synthesis as disclosed in U.S. Pat. No. 3,692,843.

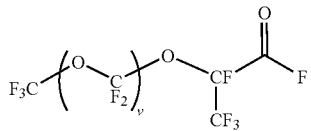

Compound D3

Other fluoroalkyl carboxylic acid derivatives, useful in preparation of compounds of formula (IV) are alkyl esters such as the methyl esters.

The term "optionally interrupted by one or more oxygens" in reference to the $R_f$ radical means that the carbon chain comprising the $R_f$ radical can be interrupted by one or more oxygen atoms, so long as the oxygens are bonded only to carbon; that is, there are no oxygen-oxygen bonds. Compounds of formula (I) wherein $R_f$ is interrupted by one or more oxygen atoms are typically derived from acyl fluorides such as D2 and D3 above.

A preferred embodiment is a compound of formula (IV) wherein $R_f$ is $C_3F_7$—; B is —O—; p is 1; and A is —$CF_3$; that is derived from treatment of compounds of formula (II) with hexafluoropropylene oxide dimer (compound D1). In a related preferred embodiment $R_o$ is $R_o^1$, as disclosed above.

Other embodiments of the invention include compositions of formula (I), herein designated as formulae (VI) and (VII), and illustrated in Scheme 2:

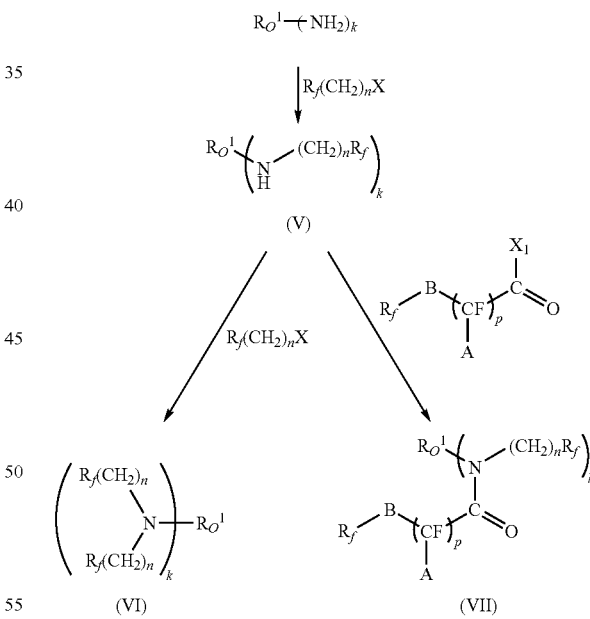

Formula (VI) is defined by formula (I) wherein X and Y are each $R_f(CH_2)_n$ and $R_o$ is $R_o^1$. Formula (VII) is defined by formula (I) wherein X is —$C(O)[CF(A)]_p$-B—$R_f$, Y is $R_f(CH_2)_n$, and $R_o$ is $R_o^1$.

Compounds of formula (VI) can be prepared by treatment of a primary monoamine, $R_o^1NH_2$; or a primary diamine, $R_o^1(NH_2)_2$; with two or four equivalents, respectively, of a perfluoroalkylalkylene halide or tosylate: $R_f(CH_2)_nX$. $R_o^1NH_2$ and $R_o^1(NH_2)_2$ preferably are the amine-terminated polyoxyalkylenes defined above. The treatment can include a solvent, for instance tetrahydrofuran (THF), and the treatment can include a base, for instance, an alkali metal carbonate.

In a similar manner, intermediate compounds of formula (V) can be prepared by treatment of a primary monoamine, $R_o^1NH_2$; or a primary diamine, $R_o^1(NH_2)_2$; with one or two equivalents, respectively, of a perfluoroalkylalkylene halide or tosylate: $R_f(CH_2)_nX$. Treatment of compounds (V) with the fluoroalkyl carboxylic acid derivatives $X_1$—C(O)[CF(A)]$_p$-B—$R_f$, in a similar manner as described for compounds of formula (IV) above, provide compounds of formula (VII). Preferred compounds of formula (VII) are wherein $R_f$ is $C_3F_7$—; B is —O—; p is 1; and A is —$CF_3$; that are derived from treatment of compounds of formula (V) with the hexafluoropropylene oxide dimer (compound D1).

The present invention further comprises a method of lowering surface tension of a medium comprising contacting the medium with a composition of formula (I) as defined above. Any of a wide variety of media are suitable for use in the method of the present invention. Typically the medium is a liquid. Examples of suitable medium include, for example, a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition of the present invention. The composition of the present invention is typically simply blended with or added to the medium. A low concentration of about 0.1% by weight of surfactant is sufficient to lower surface tension to less than about 24 mN/m, preferably less than about 22 nM/m. For many surfactants of the present invention concentrations of 0.01% by weight of the surfactant are effective to achieve a surface tension of less than about 22 mN/m.

The present invention further comprises a method of providing wetting and leveling to a coated substrate comprising adding to the coating base prior to deposition on the substrate, a composition comprising one or more compounds of formula (I) as described above. Suitable coating compositions, referred to herein by the term "coating base", include a composition, typically a liquid formulation, of an alkyd coating, Type I urethane coating, unsaturated polyester coating, or water-dispersed coating, and are described in Outlines of Paint Technology (Halstead Press, New York, N.Y., Third edition, 1990) and Surface Coatings Vol. I, *Raw Materials and Their Usage* (Chapman and Hall, New York, N.Y., Second Edition, 1984), herein incorporated by reference. Such coating bases are applied to a substrate for the purpose of creating a lasting film on the substrate surface. These are conventional paints, stains, floor polishes, and similar coating compositions.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as various classifications. Water-dispersed coatings in general contain other common coating ingredients. Water-dispersed coatings are exemplified by, but not limited to, pigmented coatings such as latex paints, unpigmented coatings such as wood sealers, stains, finishes, polishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Floor waxes, polishes, or finishes (hereinafter "floor finishes") are generally water based or solvent based polymer emulsions. The surfactants of Formula I of the present invention are suitable for use in such floor finishes. Commercially available floor finish compositions typically are aqueous emulsion-based polymer compositions comprising one or more organic solvents, plasticizers, coating aides, anti-foaming agents, surfactants, polymer emulsions, metal complexing agents, and waxes. The particle size range and solids content of the polymer are usually controlled to control the product viscosity, film hardness and resistance to deterioration. Polymers containing polar groups function to enhance solubility and may also act as wetting or leveling agents providing good optical properties such a high gloss and distinctness of reflected image.

Preferred polymers for use in floor finishes include acrylic polymers, polymers derived from cyclic ethers, and polymers derived from vinyl substituted aromatics. Acrylic polymers include various poly(alkyl acrylates), poly(alkyl methacrylates), hydroxyl substituted poly(alkyl acrylates) and poly (alkyl methacrylates). Commercially available acrylic copolymers used in floor finishes include, for example, methyl methacrylate/butyl acrylate/methacrylic acid (MMA/BA/MAA) copolymers; methyl methacrylate/butyl acrylate/acrylic acid (MMA/BA/AA) copolymers, and the like. Commercially available styrene-acrylic copolymers include styrene/methyl methacrylate/butyl acrylate/methacrylic acid (S/MMA/BA/MMA) copolymers; styrene/methyl methacrylate/butyl acrylate/acrylic acid (S/MMA/BA/AA) copolymers; and the like. Polymers derived from cyclic ethers usually contain 2 to 5 carbon atoms in the ring with optional alkyl groups substituted thereon. Examples include various oxiranes, oxetanes, tetrahydrofurans, tetrahydropyrans, dioxanes, trioxanes, and caprolactone. Polymers derived from vinyl substituted aromatics include for example those made from styrenes, pyridines, conjugated dienes, and copolymers thereof. Polyesters, polyamides, polyurethanes and polysiloxanes are also used in floor finishes.

The waxes or mixtures of waxes that are used in floor finishes include waxes of a vegetable, animal, synthetic, and/or mineral origin. Representative waxes include, for example, carnuba, candelilla, lanolin, stearin, beeswax, oxidized polyethylene wax, polyethylene emulsions, polypropylene, copolymers of ethylene and acrylic esters, hydrogenerated coconut oil or soybean oil, and the mineral waxes such as paraffin or ceresin. The waxes typically range from 0 to about 15 weight percent and preferably from about 2 to about 10 weight percent based on the weight of the finish composition.

When used as additives to a coating base or floor finish the compositions of the present invention of formula (I) as defined above are effectively introduced to the composition by thoroughly stirring it in at room or ambient temperature. More elaborate mixing can be employed such as using a mechanical shaker or providing heat or other methods. When used as an additive to coating bases or floor finishes, the compositions of the invention generally are added at about 0.001 weight % to about 5 weight % by dry weight of the composition of the invention in the wet composition. Preferably about from about 0.01 weight % to about 1 weight %, and more preferably from about 0.1 weight % to about 0.5 weight % is used.

The compounds of formula (I) are useful in many additional applications due to their surfactant properties. Examples of some applications include the following.

The compounds represented by formula (I) of the present invention are suitable for the use in fire fighting compositions, for example as a wetting agent, emulsifying agent and/or dispersion. They are also useful as a component in aqueous film forming extinguishing agents, and as an additive to dry chemical extinguishing agents in aerosol-type extinguishers, and as a wetting agent for sprinkler water.

The compounds of formula (I) of the present invention are suitable for the use in agricultural compositions. Examples include as a wetting agent, emulsifying agent and/or dispersion agent for herbicides, fungicides, weed killers, parasiticides, insecticides, germicides, bactericides, nematocides, microbiocides, defolients, fertilizers and hormone growth regulators. Formula (I) compounds are also suitable as a wetting agent for foliage, for live stock dips and to wet live stock skins; as an ingredient in sanitizing, discoloring and cleaning compositions; and in insect repellent compositions. The compounds of formula (I) are also useful as a wetting agent, emulsifying agent and/or dispersion agent for the manufacture of paper and plywood veneer. The compounds of formula (I) are also suitable for use as grease/oil repellents for paper, wood, leather, skins, metals, textiles, stone, and tiles, and as penetrant for preservative impregnation.

The compounds represented by formula (I) of the present invention are also suitable for the use as a wetting agent, emulsifying agent and/or dispersion agent for polymerization reactions, particularly polymerization of fluoromonomers. These compounds are also suitable as a latex stabilizer; as an additive for foam applications to control spreading, crawling and edge buildup; as foaming agents, as mold release agents or as demolding agents; as an internal antistatic agent and antiblocking agent for polyolefins; as a flow modifier for extruding hot melts, spreading, uniformity, anticratering; and as a retarder for plasticizer migration or evaporation in the plastics and rubber industry.

The compounds of formula (I) of the present invention are further suitable for the use in the petroleum industry as a wetting agent for oil well treatments, drilling mud; as a film evaporation inhibitor for gasoline, jet fuel, solvents, and hydrocarbons; as a lubricant or cutting oil improver to improve penetration times; as an oil spill collecting agent; and as additive to improve tertiary oil well recovery.

The compounds of formula (I) of the present invention are further suitable for the use in textile and leather industries as a wetting agent, antifoaming agent, penetrating agent or emulsifying agent; or as a lubricant for textiles, nonwoven fabrics and leather treatment; for fiber finishes for spreading, and uniformity; as a wetting agent for dyeing; as a binder in nonwoven fabrics; and as a penetration additive for bleaches. The compounds of formula (I) of the present invention are further suitable for the use in the mining and metal working industries, in the pharmaceutical industry, automotives, building maintenance and cleaning, in household, cosmetic and personal products, and in photography.

The compounds of formula (I), (II), (III), (IV), (VI) and (VII) are useful as surfactants and leveling agents in aqueous solutions and emulsions. They are further useful to alter the surface properties of such media. The compositions of the present invention have enhanced fluorine efficiency compared to current commercial products. The inventive compositions provide the advantages of altering surface properties using less fluorine to achieve the same level of performance, or provide better performance using the same level of fluorine, as prior art compositions.

Methods and Materials

The following test methods and materials were used in the Examples herein.

Test Method 1

The surface tension measurements of the surfactants were measured in fresh MILLIPORE filtered water using the Wilhelmy plate method on a Sigma70 tensiometer (KSV Instruments Inc., Monroe, Conn.) or Kruss K 11 tensiometer (Kruss USA, Matthews, N.C.) used in accordance with the manufacturers' manuals. MILLIPORE filters are available from Millipore Corporation, Billerica, Mass. The samples were initially prepared at a concentration equal to the highest concentration to be measured and diluted in the following series: 0.1, 0.01, 0.003, 0.001, 0.0003, and 0.0001 % by weight. Each concentration was automatically measured 5 times and the average and standard deviation determined by the instrument. All vessels were cleaned and rinsed thoroughly first with tap water, then deionized water, then triple rinsed with MILLIPORE filtered water. All of the vessels were cleaned by plasma for all the samples except Examples 10 and 11. Examples 10 and 11 were measured on Kruss K11 tensiometer using 50 mL sterile centrifuge tubes to prepare the samples without plasma cleaning.

Test Method 2—Wetting and Leveling Test

To test the performance of the samples in their wetting and leveling ability, the samples were added to a floor polish (RHOPLEX 3829, supplied by Rohm & Haas, Spring House, Pa., was used to prepare the final testing formulation) and applied to half of a stripped 12 inch×12 inch (30.36 cm×30.36 cm) vinyl tile. A 1% by weight solution of the surfactant to be tested was prepared by dilution in deionized water. Following the manufacturer protocols, a 100 g portion of the RHOPLEX 3829 formulation was prepared, followed by addition of 0.75 g of the 1% by weight surfactant solution, to provide a test floor polish.

The test floor polish was applied to a tile by placing 3 mL portion of the test polish in the center of the tile, and spreading from top to bottom using an applicator, and finally placing a large "X" across the tile, using the applicator. The tile was allowed to dry for 25-30 min and a total of 5 coats were applied. After each coat, the tile was rated on a 1 to 5 scale (1 being the worst, 5 the best) on the surfactant's ability to promote wetting and leveling of the polish on the tile surface. The rating was determined based on comparison of a tile treated with the floor polish that contained no added surfactant according to the following scale:

Tile Rating Scale

1 Uneven surface coverage of the film, significant streaking and surface defects 2 Visible streaking and surface defects, withdrawal of the film from the edges of the tile 3 Numerous surface defects and streaks are evident but, generally, film coats entire tile surface
4 Minor surface imperfections or streaking
5 No visible surface defects or streaks Materials Hexafluoroisobutylene (HFIB) and perfluoro-2-methyl-3-oxahexanoyl fluoride (HFPO dimer) were obtained from E.I. du Pont de Nemours and Company (Wilmington, Del.). Perfluoroethylbutyl iodide ($C_2F_5(CH_2)_4I$) and perfluorobutylbutyl iodide ($C_4F_9(CH_2)_4I$) were prepared according to the procedure disclosed in European Patent 193202.

JEFFAMINE XTJ-580 from Huntsman Chemical (The Woodlands, Tex.), also known as SURFONAMINE L-55, is a monoamine-terminated polyoxyalkylene having ethylene oxide/propylene oxide ratio of about 2.5/7.0 and a molecular weight of about 550. JEFFAMINE ED-2003 from Huntsman Chemical, also known as XTJ-502, is a polyether diamine based predominately on a polyethylene glycol backbone having about 39 PEG repeat units to about 6 propylene glycol repeat units and an approximate molecular weight of about 2000. JEFFAMINE ED-600 from Huntsman Chemical, also known as XTJ-500, is a polyether diamine based predominately on a polyethylene glycol backbone having about 9 PEG repeat units to about 3.6 propylene glycol repeat units and an approximate molecular weight of about 600. JEFFAMINE ED-900 from Huntsman Chemical, also known as XTJ-501, is a polyether diamine based predominately on a polyethylene glycol backbone having about 12.5 PEG repeat units to about 6 propylene glycol repeat units and an approximate molecular weight of about 900.

EXAMPLES

Example 1

To a mixture of isopropylamine (5.65 g) and dimethylformamide (DMF, 5 mL) was added HFIB in several portions over a period of about 0.5 h until a gentle reflux of HFIB was observed which did not dissipate. A dry-ice condenser was used to obtain the gentle reflux of HFIB at 25° C. for 15 h. The reaction mixture was poured into water (100 mL) and the bottom layer separated, washed with water (10 mL) and dried over sodium sulfate to provide N-isopropyl N-(2-trifluoromethyl-3,3,3-trifluoropropyl)amine (15 g): MS (m/e) 223 (M+, 1.2%), 208 (100%), 72 (7.8%); $^1H$ NMR (CDCl$_3$) 1.06 (d, J=6 Hz, 6H), 1.12 (m, 1H), 2.81 (m, 1H), 3.07 (m, 3H) ppm; $^{19}F$ NMR −67.0 (d, J=9 Hz) ppm.

Example 2

To a mixture of nonylamine (7.5 g) and acetonitrile (10 mL) was added HFIB in several portions over a period of about 0.5 h until a gentle reflux of HFIB was observed which did not dissipate. A dry-ice condenser was used to obtain the gentle reflux of HFIB at 25° C. for 15 h. The reaction mixture was poured into water (150 mL) and the bottom layer separated, and washed with water to provide N-nonyl N-(2-trifluoromethyl-3,3,3-trifluoropropyl)amine (13.5 g): $^1H$ NMR (CDCl$_3$) 0.88 (t, J=7 Hz, 3H), 1.28 (m, 12H), 1.47 (quintet, J=7 Hz, 2H), 2.62 (t, J=7 Hz, 2H), 3.09 (m, 3H) ppm; $^{19}F$ NMR (CDCl$_3$) −67.0 (d, J=8 Hz) ppm; MS (m/e) 307 (M+, 2.5%), 292 (0.2%), 278 (0.3%), 264 (0.5%), 250 (0.8%), 236 (0.5%), 208 (2.6%),194 (100%),156 (5.9%).

Example 3

To a mixture of 1,3-diaminopropane (3.5 g) and methanol (4 mL) was added HFIB in several portions over a period of about 0.5 h until a gentle reflux of HFIB was observed which did not dissipate. A dry-ice condenser was used to obtain the gentle reflux of HFIB at 20° C. for 15 h. The mixture was poured into water (100 mL) and the bottom layer washed with water to provide 1,3-di-(2-trifluoromethyl-3,3,3-trifluoropropylamino)propane (13 g): MS (m/e) 402 (M+, 0.5%), 251 (12%), 221 (82%), 208 (23%),194 (100%); $^1H$ NMR (CDCl$_3$): 1.66 (quintet, J=6.5 Hz, 2H), 2.72 (t, J=6.5 Hz, 4H), 3.08 (m, 6H) ppm.

Example 4

This illustrates the formation of a compound of formula (II), wherein k=1.

Sodium hydride (30 mg) was added to a mixture of Jeffamine® XT J-580 (11 g) and tetrahydrofuran (THF, 5 mL) at room temperature and the resulting mixture stirred at room temperature for 10 min. Excess HFIB was added in several portions over a period of about 0.5 h until a gentle reflux of HFIB was observed which did not dissipate. A dry-ice condenser was used to obtain the gentle reflux of HFIB at 20° C. for 1 h. The excess HFIB and THF solvent were removed under vacuum to provide the hexafluoroisobutyl amine addition product of formula (II) wherein k is 1: $^{19}F$ NMR (CDCl$_3$) at −67.0 ppm Example 5

The hexafluoroisobutyl amine addition product from Example 4 was mixed with ethyl ether (20 mL) and triethylamine (TEA, 2.5 g), followed by slow addition of HFPO dimer (6.7 g) at room temperature. The resulting mixture was stirred at room temperature overnight, and then poured into water (50 mL) and extracted with ethyl ether (100 mL). The extract was washed consecutively with water (20 mL), HCl (0.05 N, 10 mL), twice with water (20 mL), and saturated sodium chloride (20 ml), followed by concentrating and drying under vacuum to provide an oil of formula (IV) wherein k is 1:16.5 g. Surface tensions in purified water, measured using Test Method 1, are listed in Table 1. Example 5 was added to RHOPLEX 3829 floor polish and tested for wetting and leveling of the polish on a tile surface using Test Method 2. Results are listed in Table 3.

Example 6

A mixture of Jeffamine XTJ-580 (MW 550,19 g), $C_4F_9(CH_2)_4I$ (29 g, 2 equivalents), sodium carbonate (7.42 g) and DMF (30 mL) was stirred and heated at 115° C. for 15 h. The mixture was mixed with aqueous sodium chloride (10%, 200 mL) and extracted with ethyl ether (2×300 mL). The combined extracts were washed with aqueous sodium chloride (2×100 mL), concentrated and dried on vacuum to provide an oil of formula (VI), wherein k is 1: (37 g, yield 98%): $^{19}F$ NMR (CDCl$_3$) −81.5 (m, 3F), −115.0 (m, 2F), −124.9 (m, 2F), −126.5 (m,2F) ppm. Surface tension in purified water, measured using Test Method 1, is listed in Table 1. Example 6 was added to RHOPLEX 3829 floor polish and tested for wetting and leveling of the polish on a tile surface using Test Method 2. Results are listed in Table 4.

Example 7

A mixture of Jeffamine XTJ-580 (10 g), $C_2F_5(CH_2)_4I$ (12 g, 2 equivalents), sodium carbonate (4.0 g) and THF (15 mL) was heated at 80° C. for 75 h. The solids were removed by filtration and washed with ethyl ether (2×50 mL). The combined filtrate and ether washes were washed consecutively with water (2×50 mL), and saturated sodium chloride (50 mL), concentrated and dried on vacuum to give an oil (11.0 g, yield 67%) of formula (VI), wherein k is 1: $^{19}$F NMR (CDCl$_3$) −85.9 (s, 3F), −118.6 (t, J=18 Hz, 2F) ppm. Surface tensions in purified water, measured using Test Method 1, are listed in Table 1.

Example 8

A mixture of Jeffamine XTJ-580 (10 g), the iodide C$_2$F$_5$(CH$_2$)$_4$I (5.6 g, 1 equivalent), sodium carbonate (2.2 g) and THF (15 mL) was heated at 35° C. for 15 h and 80° C. for 8 h. The liquid was decanted into another flask and about 1 g of the liquid was concentrated to give the monoalkyl addition product of formula (V) as an oil for analysis. TEA (1.8 g) was added to the remainder of the liquid and the liquid cooled to 10° C. with an ice-water bath. HFPO dimer (6.1 g) was slowly added at 10-25 ° C. followed by stirring at room temperature for 3 h. The mixture was poured into water (200 mL) and extracted with ethyl ether (2×150 mL). The combined ether extracts were washed with water (2×50 mL) and saturated sodium chloride (20 mL), concentrated and dried on vacuum to give an oil (15.3 g, yield 81%) of formula (VII), wherein k is 1. Surface tensions in purified water, measured using Test Method 1, are listed in Table 1.

Example 9

To a mixture of ED-600 (10.3 g), THF (20 ml), and TEA (0.5 g) was added HFIB in several portions over a period of about 0.5 h until a gentle reflux of HFIB was observed which did not dissipate. A dry-ice condenser was used to obtain the gentle reflux of HFIB at 10-20° C. for 3.5 h. The excess HFIB and solvent were removed under vacuum to provide an oil: $^{19}$F NMR (CDCl$_3$) at −67.0 ppm.

To a mixture of the above oil and TEA (3.06 g) was slowly added HFPO dimer (10.5 g) at room temperature over 30 min. The resulting mixture was stirred at room temperature overnight and poured into water (75 mL) and extracted with ethyl ether (150 mL). The ether extract was washed with 5 weight % sodium hydrogen carbonate solution to pH=~7; then washed with saturated sodium chloride (20 mL); dried over anhydrous sodium sulfate; and concentrated on vacuum to give an oil (23.8 g) of formula (IV), wherein k is 2. Maldi MS analysis indicated the formation of desired products. Surface tension in MILLIPORE filtered water, prepared by sonification of the aqueous sample using a Branson 3510 sonicator (Branson Ultrasonics Corp., Danbury, Conn.), as measured using Test Method 1, is listed in Table 1.

Example 10

To a mixture of ED-900 (10.7 g), THF (20 ml), and TEA (0.5 g) was added HFIB in several portions over a period of about 0.5 h until a gentle reflux of HFIB was observed which did not dissipate. A dry-ice condenser was used to obtain the gentle reflux of HFIB at 10-20° C. for 3.5 h. The excess HFIB and solvent were removed under vacuum to provide an oil: $^{19}$F NMR (CDCl$_3$) at −67.0 ppm.

To a mixture of the above oil and TEA (2.22 g) was slowly added HFPO dimer (7.75 g) at room temperature over 30 min. The resulting mixture was stirred at room temperature overnight and poured into water (75 mL) and extracted with ethyl ether (150 mL). The resulting mixture separated into three layers. The top layer was isolated, washed with 5 weight % sodium hydrogen carbonate solution to pH=~7 and then with saturated sodium chloride (20 mL); dried over anhydrous sodium sulfate; and concentrated on vacuum to give an oil (17.2 g) of formula (IV), wherein k is 2. Maldi MS analysis indicated the formation of desired products. Surface tension in MILLIPORE filtered water, prepared by sonification of the aqueous sample using a Branson 3510 sonicator, as measured using Test Method 1, is listed in Table 1.

Comparative Example A

Comparative Example A consisted of a fluoroalkyl ethoxylate surfactant (commercially available from E. I. du Pont de Nemours and Company, Wilmington, Del.), containing a mixture of ethoxylated perfluoroalkyl homologues ranging from 2 to 16 carbon atoms, predominantly 6, 8 and 10 carbon atoms. The surface tension was measured in MILLIPORE filtered water using Test Method 1. The results are listed in Table 1. Comparative Example A was added to RHOPLEX 3829 floor polish and tested for wetting and leveling of the polish on a tile surface using Test Method 2. Results are listed in Table 3.

Comparative Example B

Comparative Example B was a commercial surfactant available from E. I. du Pont de Nemours and Company, Wilmington, Del. containing a mixture of ethoxylated perfluoroalkyl homologues ranging from 2 to 16 carbon atoms, predominantly 6, 8 and 10 carbon atoms. The level of ethoxylation is higher than in Comparative Example A. The surface tension was measured in MILLIPORE filtered water using Test Method 1. The results are listed in Table 1. Comparative Example B was added to RHOPLEX 3829 floor polish and tested for wetting and leveling of the polish on a tile surface using Test Method 2. Results are listed in Table 4.

TABLE 1

| Concentration (weight %) | Surface Tension (mN/m) Example | | | | | | | |
|---|---|---|---|---|---|---|---|---|
| | 5 | 6 | 7 | 8 | 9 | 10 | Comparative A | Comparative B |
| 0 | 71.6 | 71.6 | 71.6 | 71.0 | 72.4 | 72.2 | 70.91 | 71.54 |
| 0.0001 | 69.99 | 53.76 | 66.9 | 71.41 | 65.9 | 58.6 | 72.14 | 70.97 |
| 0.0003 | 26.65 | 34.19 | 51.2 | 52.32 | | | 69.11 | 64.54 |
| 0.001 | 21.68 | 27.27 | 44.33 | 25.11 | 41.6 | 31.8 | 41.14 | 45.45 |
| 0.003 | 20.51 | 24.68 | 37.84 | 21.92 | | | 27.92 | 31.04 |
| 0.01 | 20.65 | 21.01 | 28.68 | 21.43 | 32.9 | 22.3 | 21.04 | 25.75 |
| 0.02 | | | | | 21.8 | 20.9 | | |
| 0.1 | 19.68 | 20.69 | 24.11 | 21.26 | | | | 21.99 |

Comparison of the surface tensions of Examples 5-10 with Comparative Examples A and B indicated that the Examples 5-10 exhibited surface tensions generally lower at very low concentrations of 0.0001 and 0.0003. As the concentrations increase the surface tensions of Examples 5-10 are comparable to Comparative Examples A and B, but still much lower than pure water indicating useful surfactant properties.

Table 2 below compares the performance of the surfactants of Examples 5-10 with Comparative example A and B in terms of weight % concentration needed to lower the surface tension of water to 22 mN/m or below; as well as the % fluorine required to lower the surface tension of water to 22 mN/m or below.

TABLE 2

Concentration of surfactant to achieve surface tension of 22 mN/m

| Example | Concentration (weight %) | % F ($\times 10^{-4}$) |
|---|---|---|
| Comparative A | 0.01 | 46 |
| Comparative B | 0.10 | 500 |
| 5 | 0.001 | 3.1 |
| 6 | 0.01 | 31 |
| 7[a] | 0.01 | 211 |
| 8 | 0.003 | 8.8 |
| 9 | 0.02 | 85 |
| 10 | 0.02 | 70 |

[a] to achieve a minimum surface tension of 24 mN/m.

The data in Table 2 indicates that Examples 5, 6 and 8 achieved a desired surface tension of below 22 mN/m at a lower % fluorine than Comparative Example A and B. All the Examples of the invention, with the exception of Example 7, achieved a desired surface tension of below 22 mN/m at a lower % fluorine than Comparative Example B. Example 7 provided a minimum surface tension of 24 mN/m suggesting that compounds of formula (VI) function as surfactants, but are less preferred.

TABLE 3

Ratings for Wetting and Leveling Test

| Example | \multicolumn{5}{c}{Rating Coating No.} | |
|---|---|---|---|---|---|---|
| | 1 | 2 | 3 | 4 | 5 | average |
| Control[a] | 2 | 2 | 1 | 1 | 1 | 1.4 |
| Comparative A | 3 | 4 | 4 | 4 | 4 | 3.8 |
| 5 | 4 | 4.5 | 4.5 | 4.5 | 4 | 4.3 |

[a] with no additive, exhibited orange peel effect after the 2nd coat.

The data in Table 3 indicates that Example 5 performance is better than the Comparative Example A for enhancing wetting and leveling in floor polish.

Comparative Example C

Comparative Example C was a commercial surfactant available from E. I. du Pont de Nemours and Company, Wilmington, Del. containing a mixture of ethoxylated perfluoroalkyl homologues ranging from 2 to 16 carbon atoms, predominantly 6, 8 and 10 carbon atoms, in ethylene glycol and water. Comparative Example C contains the same level of ethoxylation as Comparative Example A, but is in a solvent of ethylene glycol and water. Comparative Example C was tested for performance in wetting and leveling ability in commercial floor polish according to Test Method 2. The results are listed in Table 4.

TABLE 4

Ratings for Wetting and Leveling Test

| Example | \multicolumn{5}{c}{Rating Coating No.} | |
|---|---|---|---|---|---|---|
| | 1 | 2 | 3 | 4 | 5 | average |
| Control[a] | 2 | 2 | 1 | 1 | 1 | 1.4 |
| Comparative B | 2 | — | 4 | 4 | 4 | 3.5 |
| 6 | 3 | — | 4 | 4.5 | 4 | 3.9 |

[a] with no additive, exhibited orange peel effect after the 2nd coat.

The data is Table 4 indicates that Example 6 exhibited performance better than the Comparative Example C.

What is claimed is:

1. A compound of formula (I):

wherein
k is 1 or 2;
Y is —$CH_2CH(CF_3)_2$ or —$(CH_2)_nR_f$;
X is hydrogen, —$(CH_2)_nR_f$, or —$C(O)[CF(A)]_p$—B—$R_f$;
B is a divalent radical selected from the group consisting of a covalent bond, —O— and —$(CH_2)_m$—;
m is an integer of 1 to about 10;
p is an integer of 0 or 1, with the proviso that when p is 0, B is a covalent bond or —$(CH_2)_m$—;
n is an integer of from about 3 to about 10;
A is —F or —$CF_3$;
each $R_f$ is independently $C_1$ to $C_6$ perfluorinated linear or branched alkyl, optionally interrupted by one or more oxygens;
$R_o$ is $R_o^1$ or is a linear or branched alkyl having from about 10 to about 100 carbon atoms, interrupted or substituted by one or more hydrophilic groups selected from the group consisting of —O—, —OH, —NR—, —$N(R)_2$, and —C(O)NR—, wherein a) the ratio of hydrophilic groups to carbon atoms is from about 1:2 to about 1:10; b) each carbon atom has at most one hydrophilic group bonded to it, and c) covalent bonding between hydrophilic groups is absent;
R is hydrogen or a $C_1$ to $C_4$ linear or branched alkyl; and
$R_o^1$ is a linear or branched aliphatic group of from about 10 to about 100 carbon atoms, interrupted by about from about 5 to about 50 ether oxygens, wherein a) the ratio of ether oxygen to carbon atoms is from about 1:2 to about 1:3, b) each carbon atom has at most one ether oxygen atom bonded to it, and c) covalent bonding between ether oxygen atoms is absent;
provided that
1) when Y is —$(CH_2)_nR_f$, $R_o$ is $R_o^1$;
2) when X is hydrogen, Y is —$CH_2CH(CF_3)_2$; and
3) when X is —$(CH_2)_nR_f$ and Y is —$(CH_2)_nR_f$, $R_o$ is $R_o^1$.

2. The compound of claim 1 wherein X is H and Y is —$CH_2CH(CF_3)_2$.

3. The compound of claim 1 wherein X is —$(CH_2)_nR_f$ and Y is —$CH_2CH(CF_3)_2$.

4. The compound of claim 1 wherein X is —$C(O)[CF(A)]_p$-B—$R_f$ and Y is —$CH_2CH(CF_3)_2$.

5. The compound of claim 1 wherein $R_o$ is $R_o^1$.

6. The compound of claim 4 wherein $R_f$ is $C_3F_7$—; B is —O—; p is 1; and A is —$CF_3$.

7. The compound of claim 1 wherein X is —$(CH_2)_nR_f$, Y is —$(CH_2)_nR_f$, and $R_o$ is $R_o^1$.

8. The compound of claim 1 wherein X is —C(O)[CF(A)]$_p$-B—$R_f$, Y is —$(CH_2)_nR_f$, and $R_o$ is $R_o^1$.

9. The compound of claim 8 wherein $R_f$ is $C_3F_7$—; B is —O—; p is 1; and A is —$CF_3$.

10. A method of lowering surface tension of a medium comprising contacting the medium with a composition of formula (I)

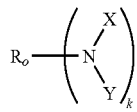

(I)

wherein
k is 1 or 2;
Y is —$CH_2CH(CF_3)_2$ or —$(CH_2)_nR_f$;
X is hydrogen, —$(CH_2)_nR_f$, or —C(O)[CF(A)]$_p$—B—$R_f$;
B is a divalent radical selected from the group consisting of a covalent bond, —O— and —$(CH_2)_m$—;
m is an integer of 1 to about 10;
p is an integer of 0 or 1, with the proviso that when p is 0, B is a covalent bond or —$(CH_2)_m$—;
n is an integer of from about 3 to about 10;
A is —F or —$CF_3$;
each $R_f$ is independently $C_1$ to $C_6$ perfluorinated linear or branched alkyl, optionally interrupted by one or more oxygens;
$R_o$ is $R_o^1$ or is a linear or branched alkyl having from about 10 to about 100 carbon atoms, interrupted or substituted by one or more hydrophilic groups selected from the group consisting of —O—, —OH, —NR—, —N(R)$_2$, and —C(O)NR—, wherein a) the ratio of hydrophilic groups to carbon atoms is from about 1:2 to about 1:10; b) each carbon atom has at most one hydrophilic group bonded to it, and c) covalent bonding between hydrophilic groups is absent;

R is hydrogen or a $C_1$ to $C_4$ linear or branched alkyl; and $R_o^1$ is a linear or branched aliphatic group of from about 10 to about 100 carbon atoms, interrupted by about from about 5 to about 50 ether oxygens, wherein a) the ratio of ether oxygen to carbon atoms is from about 1:2 to about 1:3, b) each carbon atom has at most one ether oxygen atom bonded to it, and c) covalent bonding between ether oxygen atoms is absent;

provided that
1) when Y is —$(CH_2)_nR_f$, $R_o$ is $R_o^1$;
2) when X is hydrogen, Y is —$CH_2CH(CF_3)_2$; and
3) when X is —$(CH_2)_nR_f$ and Y is —$(CH_2)_nR_f$, $R_o$ is $R_o^1$.

11. The method of claim 10 wherein the medium is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent.

12. The method of claim 11 wherein the medium is a floor polish.

13. The method of claim 10 wherein the lowering of surface tension enhances wetting and leveling of the medium on a floor.

* * * * *